(12) United States Patent
Desrochers et al.

(10) Patent No.: US 7,389,158 B2
(45) Date of Patent: Jun. 17, 2008

(54) METHOD OF MAKING COMPARISONS OF INDOOR AIR QUALITY SCORES

(75) Inventors: Eric M. Desrochers, Millis, MA (US); Gordon P. Sharp, Newton, MA (US)

(73) Assignee: Aircuity, Inc., Newton, MA (US)

( * ) Notice: Subject to any disclaimer, the term of this patent is extended or adjusted under 35 U.S.C. 154(b) by 0 days.

(21) Appl. No.: 11/391,105

(22) Filed: Mar. 28, 2006

(65) Prior Publication Data

US 2006/0173580 A1 Aug. 3, 2006

Related U.S. Application Data

(62) Division of application No. 09/779,379, filed on Feb. 7, 2001, now Pat. No. 7,302,313.

(51) Int. Cl.
*G05B 21/00* (2006.01)
*G01N 7/00* (2006.01)

(52) U.S. Cl. .................. 700/277; 700/49; 700/276; 706/930; 73/31.02

(58) Field of Classification Search ............... 700/276, 700/49, 277; 706/930, 931
See application file for complete search history.

(56) References Cited

U.S. PATENT DOCUMENTS 5,742,516 A * 4/1998 Olcerst ................. 700/276
6,711,470 B1 * 3/2004 Hartenstein et al. ........ 700/276
7,302,313 B2 * 11/2007 Sharp et al. ............. 700/276

OTHER PUBLICATIONS

Apte, Michael G.; Fisk, William J.; Daisey, Joan M. "Associations Between Indoor CO[sub2] Concentrations and Sick Building Syndrome Symptoms in U.S. Office Buildings: An Analysis of the 1994-1996 BASE Study Data." Indoor Air 10.4 (Dec. 2000): 246-257.*
Nakai, Satoshi; Nitta, Hiroshi; Ono, Masaji; Abe, Keiko; Sakaguchi, Masahiro. "Measurements of Biological Contaminants and Particulate Matter Inside a Dwelling in Japan." Indoor Air 9.1 (Mar 1999): 41-46.*

* cited by examiner

*Primary Examiner*—Ryan A Jarrett
(74) *Attorney, Agent, or Firm*—Brian M. Dingman; Mirick, O'Connell, DeMallie & Lougee, LLP

(57) ABSTRACT

An air monitoring system is disclosed having an air monitoring unit with at least one sensor for measuring data of an air quality parameter and a computer for storing the air quality parameter data received from the sensor. The air monitoring unit may use an installed or a portable system, or a combination of both, for measuring the air quality parameters of interest. A remote data center may be provided, and the data may be uploaded to the data center from the unit by a communications media such as the Internet. Information or instructions may also be downloaded from the data center to the unit via the communications media for controlling or modifying the function of the unit. An expert system may be provided with the air monitoring system for controlling the unit. The information or instructions downloaded to the unit may be generated by the expert system.

19 Claims, 10 Drawing Sheets

METHOD OF MAKING COMPARISONS OF INDOOR AIR QUALITY SCORES

CROSS REFERENCE TO RELATED APPLICATION

This application is a divisional from U.S. Nonprovisional application No. 09/779,379, filed on Feb. 7, 2001 now U.S. Pat. No. 7,302,313 from which this divisional claims the benefit of priority.

FIELD OF THE INVENTION

This invention relates to air quality monitoring systems and methods. More particularly, this invention relates to an air monitoring system that is customized for a specific structure, such as a building or a home, and/or the occupants. Still more particularly, the air monitoring system measures certain air quality parameters and may provide an analysis of the data collected and may make recommendations for improving the air quality parameters.

BACKGROUND OF THE INVENTION

Over time people have become more energy-conscious. Because of this, the construction industry started building structures that are far "tighter" than their predecessors, with respect to air leakage. Buildings are now carefully designed to provide occupants with a precisely metered exchange between indoor and outdoor air. The exchange between indoor and outdoor air is selected to provide a healthy quality of indoor air, with a minimum of energy usage for heating or cooling the outdoor air introduced into the building. However, inevitably the tradeoff sometimes results in unacceptable indoor air quality. Moreover, the use of new building materials having many superior and desirable properties in both renovations of old buildings and new construction sometimes aggravates the air quality problems because the building materials outgas undesirable substances.

With respect to air quality in the home or in schools, incidence rate of asthma, which is often triggered by poor indoor air quality, is growing exponentially. It has more than doubled since the eighties, with the current level of 17 million American sufferers projected to double again in two decades. A recent national survey reported that 56% of all households now contain at least one member with allergies or asthma. In all, over 90 million Americans are reported sufferers of asthma or allergies, with direct costs of about $19 billion annually for medical care, pharmaceuticals, and asthma and allergy products. For example, air cleaners are now one of the fastest growing household products, with over 16 million households using at least one unit. Particular aspects of indoor air quality are a concern, such as toxic molds, dust mites, carbon monoxide poisoning, allergens, and various chemical pollutants.

With respect to air quality in commercial or industrial environments, the U.S. Environmental Protection Agency (EPA) estimates that one-third of the 4.5 million commercial buildings in the U.S. offer less than acceptable air quality. The EPA has also stated that indoor air quality is one of the top five environmental health risks of our time. Business Week in its lead cover story of Jun. 5th, 2000, "Is Your Office Killing You? The dangers of sick buildings", reported that U.S. companies could save as much as $258 billion annually by preventing sick-building illnesses and improving worker performance by creating offices with better indoor air.

Thus, indoor air quality is an issue of great importance in residential, commercial and industrial environments. Before the air quality in these environments can be improved, it should be first measured and evaluated to determine if a problem exists and then diagnosed to evaluate the nature of the problem. Unfortunately, it is currently very expensive to obtain a customized indoor air quality assessment of a building plus a customized set of recommendations to solve any potential air quality problems uncovered. To accomplish this today requires the use of costly, hard to apply instruments and the expertise of relatively expensive industrial hygiene professionals.

As an affordable alternative, building owners and occupants can explore books and websites having generalized information on air quality. However, without indoor air quality expertise to evaluate a specific building's situation, this generalized information is of only limited value. Similarly, instruments can be rented to take specific measurements, but this can be very time consuming and expensive. Moreover, useless data can be generated without properly taking into account building specific data and information to properly set up the instruments and determine where and when to run a test. Furthermore, without monitoring, analyzing and adapting the data taking process in real time, based on the real time data from the instruments, important events and trends can easily be missed. Additionally, problems in the instruments or their locations can render a whole series of measurements useless. These functions are traditionally supplied by the industrial hygiene professional, who provides a personalized assessment of the indoor air environment.

Beyond the use of an industrial hygienist employing sophisticated air measurement instruments, there have been only limited options to help the building owner or occupant obtain information about the air quality of their environment. One such device is described in U.S. Pat. No. 5,553, 006. This patent discloses a system that is limited to gathering air quality data and transmitting the data through a network, serial interface or phone line to a user. There are also systems, as discussed in U.S. Pat. No. 5,892,690, that gather air quality data from a building and then send the data through the Internet to a customer accessible website, where it is archived and available to the customer in graphically displayed form. Although convenient for a customer, there is no analysis of the data, nor is there any way for the system to adapt its operation or to be customized automatically based on the specific building being measured or the data that is gathered. U.S. Pat. No. 6,125,710 discloses a networked air measurement system and describes a method for inexpensively gathering air quality or environmental data. However, it does not describe any methods for customizing the data taking process to a given building or analyzing the data that is taken.

Some available devices measure and data log some environmental air parameters and then send emails to a customer based on predetermined levels being exceeded, but do not take into account anything more sophisticated in their analysis of the data. Nor do these devices employ any method to reprogram or modify the testing program remotely.

U.S. Pat. No. 4,226,115 describes an outdoor air monitoring device, held aloft by a balloon, that employs remote radio wave communication for triggering the taking of a sample of ambient air. However, this device is not designed for indoor use, requires intervention of a trained operator to decide when to take the sample and involves expensive technology with limited range due to the use of radio wave communication for transmission to the device.

None of the prior art disclosed provides the user with customized information and recommendations about the air quality within or immediately around a specific building. As such, there is a need for an economical, easy to use system to provide customized, understandable and easily accessible information to a building owner or occupant. Also, there is a need for a system that can properly diagnose air quality problems and recommend solutions without requiring the expense of an industrial hygiene professional.

SUMMARY OF THE INVENTION

The air monitoring system of the invention may be a portable or installed system, or may have one or more permanently installed components and one or more portable components. The air monitoring system includes an air monitoring unit. The air monitoring unit may be a portable unit, such as a handheld unit or a reasonably portable unit, containing one or more sensors for acquiring data on certain air quality parameters. The unit may be moved indoors to acquire data on certain air quality parameters in desired locations in a building and may also be moved outdoors around the building to acquire data on certain environmental and air quality parameters of interest. The portable unit may log the sensor data and communicate it to the user through a direct local interface or through the Internet.

The installed system may be an air monitoring unit that is installed in a building to monitor one or more spaces. If monitoring multiple spaces, the air monitoring unit may use one or more individual sensor units which contain one or more different sensors that are distributed inside or outside a building to monitor environmental and other air quality parameters of interest. These remotely distributed sensor units communicate with a central unit through a digital network or other communication link such as a power line or wireless communication. The central unit logs the sensor data and communicates the data to the user through a direct local interface or through the Internet.

Alternatively, the air monitoring unit may contain sensors, and a multiple tube and vacuum system may be used to transport samples of air to the air monitoring unit from one or more remotely located sampling locations. This air monitoring system may involve a star based tube structure or "octopus" type arrangement that uses many tubes each making a "home run" from the sampling location to the air monitoring unit. Another option is to use a networked air sampling system that includes a common centrally located air monitoring unit containing one or more sensors. This system, as described in U.S. Pat. No. 6,125,710 and incorporated herein by reference, involves a common backbone tube with branches, so that multiple packets of air are routed through the same backbone from multiple locations.

As stated previously, the air monitoring unit may be connected to the direct local interface or to the Internet. The connection of the air-monitoring unit to the Internet can be achieved in one of several ways. A direct local connection to the building's data network, assuming the building has such a network, can be used. A common network in use within commercial facilities is an Ethernet system. Assuming this network has a connection to the Internet, the network may be used as a connection to the Internet. Another method employs a local wireless connection or other systems that are commonly used in cordless phones. This involves a base unit transceiver that connects to a local phone line in the building and another transceiver in the air monitoring unit. When the unit needs to send or receive data, the unit checks the phone line to determine if it is busy, and if not the unit makes a call and sends or receives data through a local Internet Service Provider (ISP). Another method is to use a cellular phone to directly access a local or remote ISP. Finally, the monitoring unit may connect to a building control network in the building, which is connected to the Internet. It will be understood that any method of connecting to the Internet may be used.

A portable unit may incorporate Global Positioning System (GPS) technology. This allows the precise location of the air monitoring unit to be determined. Use of GPS technology eliminates the need for the operator to input the unit location, and permits the location data to be stored and associated with the proper building and room within that building. The test location is one type of information used to customize the analysis of the air monitoring system, so that the analysis applies to the specific building that is being monitored.

The air monitoring system may use an expert system to analyze air quality information for a variety of purposes. The expert system may operate the air monitoring unit and analyze the results of tests with respect to a specific building or room. The expert system may include a program or a combination of programs that uses rule based, case based or pattern recognition methods or a combination of these methods to analyze data and make decisions and recommendations based on user supplied information, environmental data, such as weather, and measured air quality data. Alternatively, or in addition, the expert systems, sometimes referred to as artificial intelligence (AI) systems, may use fuzzy logic, neural networks or other AI techniques to analyze data or make decisions. The basis of the rules on which the expert system is founded may be a combination of knowledge supplied by experts and experience that the system achieves through feedback as to the accuracy of its analysis or decisions.

The Internet may be used to download information from a website to the air monitoring unit to change its program, operation, and/or setup based on specific information obtained about the building, its occupants and its surrounding environment. This customization of the unit may be achieved by an expert system located remotely or in the air monitoring unit. Preferably, customization of the unit is achieved through the Internet due to the ease and simplicity of using a web browser on an Internet website. This aspect of the invention may involve the user answering questions about the building on the website. The information may then be used to create a customized monitoring program to analyze the specific building, particularly upon initial setup of the air monitoring system. This program is then downloaded into the memory of the monitoring unit to control its operation. As air quality parameter data is acquired in and around the building, the program, operation and/or setup of the monitoring unit may be modified or updated based on the measured data. Alternatively, non-expert system approaches may be used to customize the unit based on building specific information. However, an expert system provides customization based on an expert system's ability to process information in a way that simulates a human expert.

For example, the expert system may be used to analyze the data in real time and to modify the monitoring protocol in order to perform a better analysis. One such change in monitoring may be the expert system triggering the taking of a grab sample based on a real time analysis of the acquired data.

A modular structure for an air monitoring unit may utilize centrally located sensors. For example, the unit may use a card cage or sensor bay configuration, with the sensors mounted on cards that slide into a card cage or sensor bay in the air monitoring unit. Depending on specific needs or potential problems in a building, the unit may be customized with various sensors. The selection of the sensors may be based on a reported problem, questions answered by the user or may be generated by the expert system using more sophisticated analysis of additional information.

For better understanding of the overall quality of air in a building or in its immediate surrounding, an "IAQ Index" that involves a weighted combination of more than one air quality parameter can be used. The score of the particular building may be compared to the scores of other buildings of like type or in a similar environment or location to give a percentage score from 0 to 100% that indicates where the specified building falls in comparison to the other buildings in the comparison set. Information can then be provided to help a user increase the score with specific recommendations that will provide solutions to improving those air quality parameters on which the specified building had a low score.

According to one aspect of the invention, an air monitoring system is provided. The air monitoring system comprises an air monitoring unit having at least one sensor for acquiring air quality parameter data, and a computer having an expert system for controlling the air monitoring unit based at least in part on the acquired air quality data.

According to another aspect of the invention, an air monitoring system is provided. The air monitoring system comprises an air monitoring unit having at least one sensor for measuring air quality parameter data. The air monitoring unit is adapted to download information from a remote data center through a communication link to modify the function of the air monitoring unit.

According to another aspect of the invention, an air monitoring system is provided. The air monitoring system comprises an air monitoring unit having at least one sensor for measuring air quality parameter data and a computer for storing the data received from the sensor. A remote data center includes a database for storing the air quality parameter data and receiving inputted characteristics and an expert system that interacts with the air quality parameter data for analysis of the data in relation to the certain inputted characteristics. A communication link is provided between the data center and the air monitoring unit. The remote data center downloads information to the air monitoring unit through the communication link to modify the function of the air monitoring unit.

According to another aspect of the invention, an air monitoring unit comprises at least one removable card having at least one sensor and a shroud enclosing the sensor, and a conduit connected to the shroud.

According to another aspect of the invention, an air monitoring system comprises an air monitoring unit including a grab sampler contained within the air monitoring unit for acquiring an air sample. A remote control unit controls the air monitoring unit, and a communications link is provided between the control center and the air monitoring unit. The control unit is adapted to download a command to the air monitoring unit to trigger the grab sampler to acquire an air sample.

According to another aspect of the invention, an apparatus comprises an air monitoring system having at least one sensor for acquiring air quality data at a selected indoor location and a computer including an expert system for analyzing the acquired air quality data and reaching a conclusion regarding air quality of the selected indoor location.

According to another aspect of the invention, an apparatus comprises an air monitoring system having at least one sensor for acquiring air quality data at a selected indoor location and a control site for controlling operation of the air monitoring system through the Internet.

According to another aspect of the invention, a method for monitoring indoor air quality comprises the steps of providing information representative of a selected indoor location to a remotely located control unit, positioning an air quality monitoring unit in the selected indoor location downloading customized operating information from the control unit to the air quality monitoring unit, and monitoring the air quality at the selected location in accordance with the customized operating information.

According to another aspect of the invention, a sensor card for use in an air quality monitoring system comprises a card having a connector for electrical connection to the air quality monitoring system and an air quality sensor mounted on the card for providing sensor data through the connector to the air quality monitoring system.

According to another aspect of the invention, an air quality monitoring system comprises at least one air quality sensor for acquiring sensor data at a selected indoor location, a control unit for generating a grab sample command in response to the acquired sensor data meeting a predetermined criteria, and a grab sample unit for acquiring an air sample at the selected indoor location in response to the grab sample command from the control unit.

According to another aspect of the invention, an air quality monitoring unit comprises a housing, a plurality of easily removable air quality sensors mounted in said housing, and a programmable control unit having an interface to the air quality sensors. The control unit is programmable so as to customize the air quality monitoring unit for operation with different sensors.

The foregoing aspects of the invention may be utilized separately or in any combination.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS

Figure 1A:
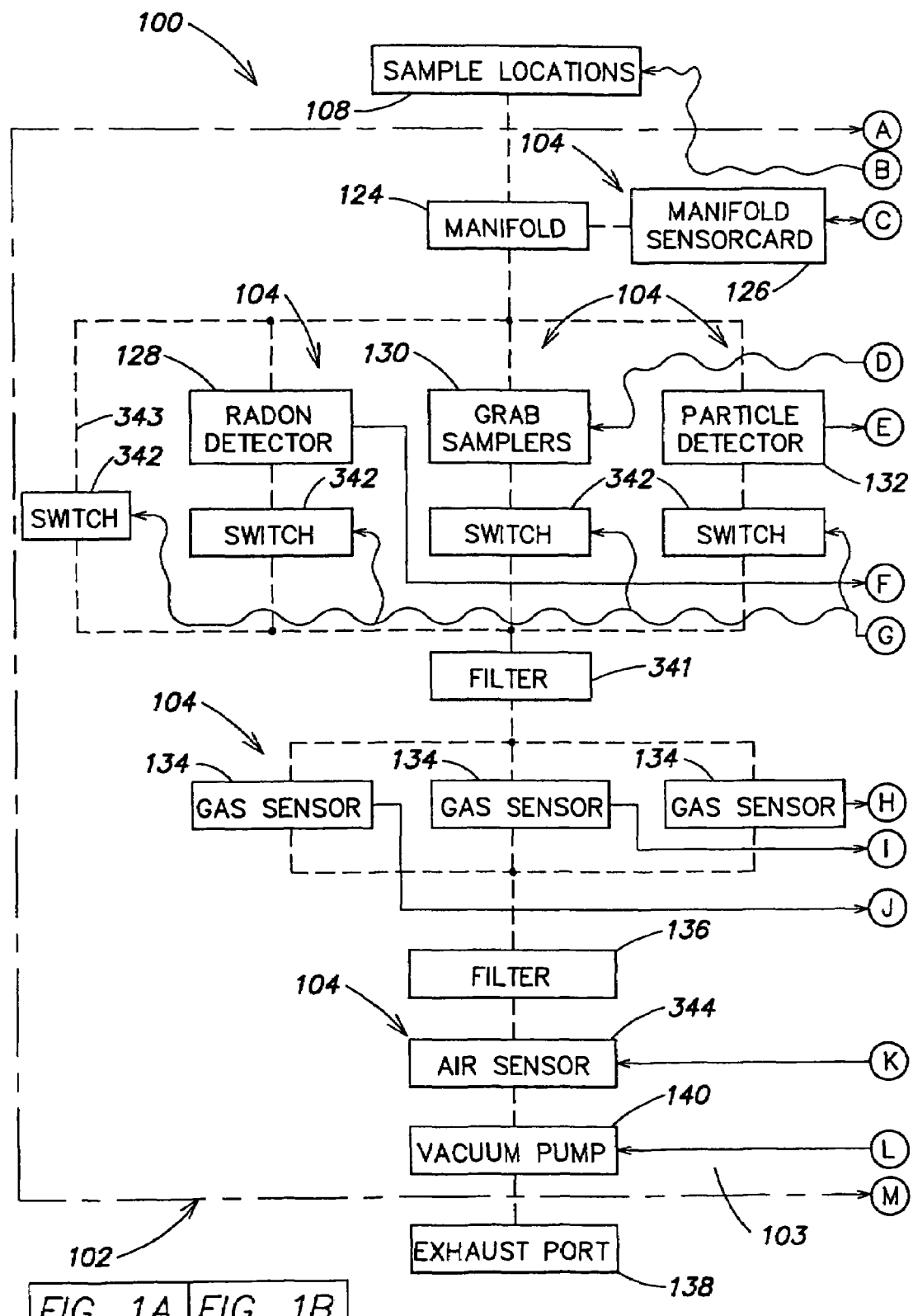
FIG. 1 is a schematic block diagram of an air monitoring system according to an embodiment of the invention.
Figure 1B:
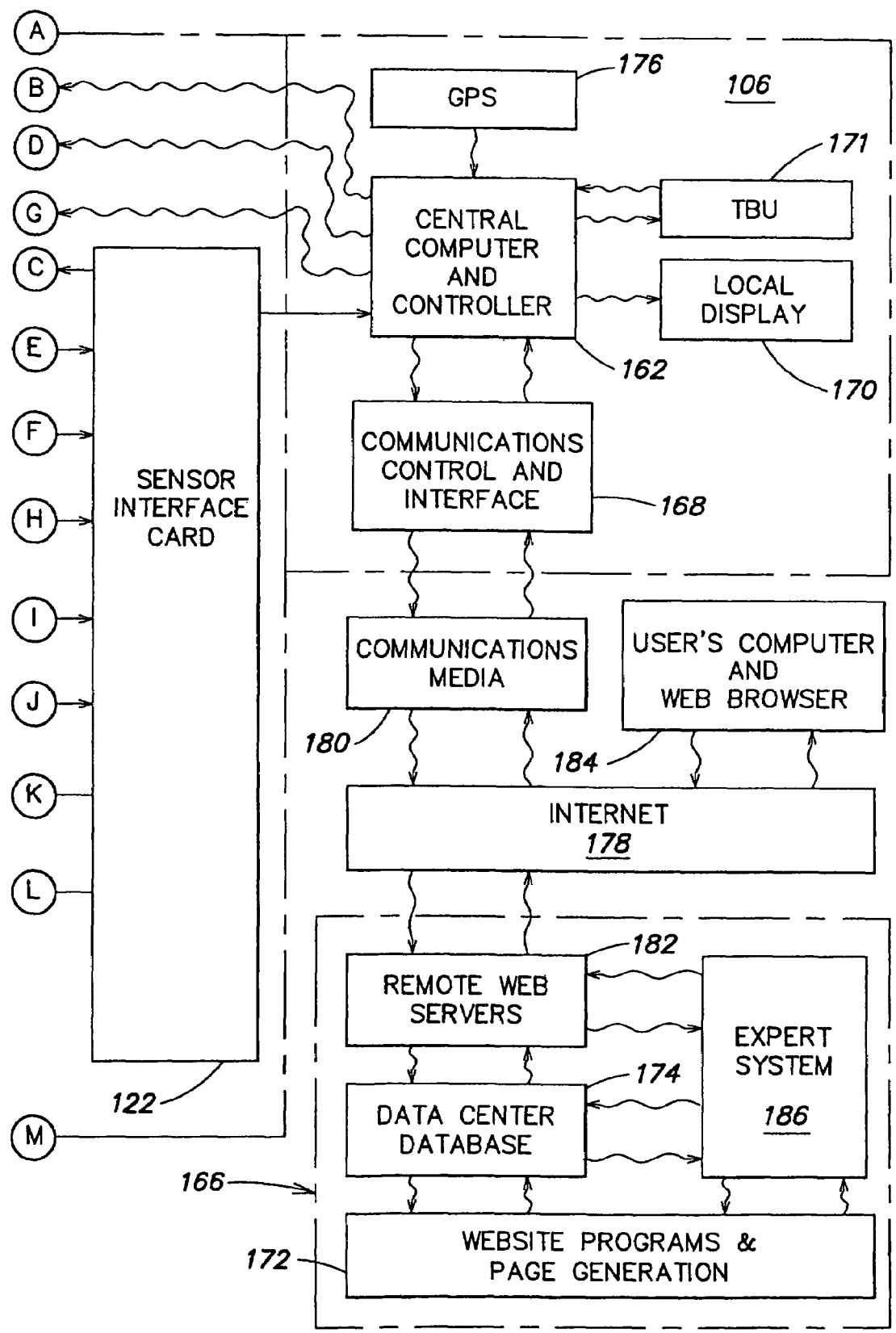

Referring to FIG. 1, a schematic block diagram of one embodiment of an air monitoring system 100 according to the present invention is shown. The air monitoring system may be a portable or an installed system, or a system having a combination of portable and installed components. The air monitoring system 100 includes an air monitoring unit 102.

In a portable system, the air monitoring unit 102 may be hand held or reasonably portable. The air monitoring unit includes a sensor unit 103 having at least one sensor 104 and a control unit 106. In a portable system the air to be sampled, or sample locations 108, may be taken from the area immediately surrounding the air monitoring unit or through a tube (not shown) from one or more remote sample locations.

Figure 2:
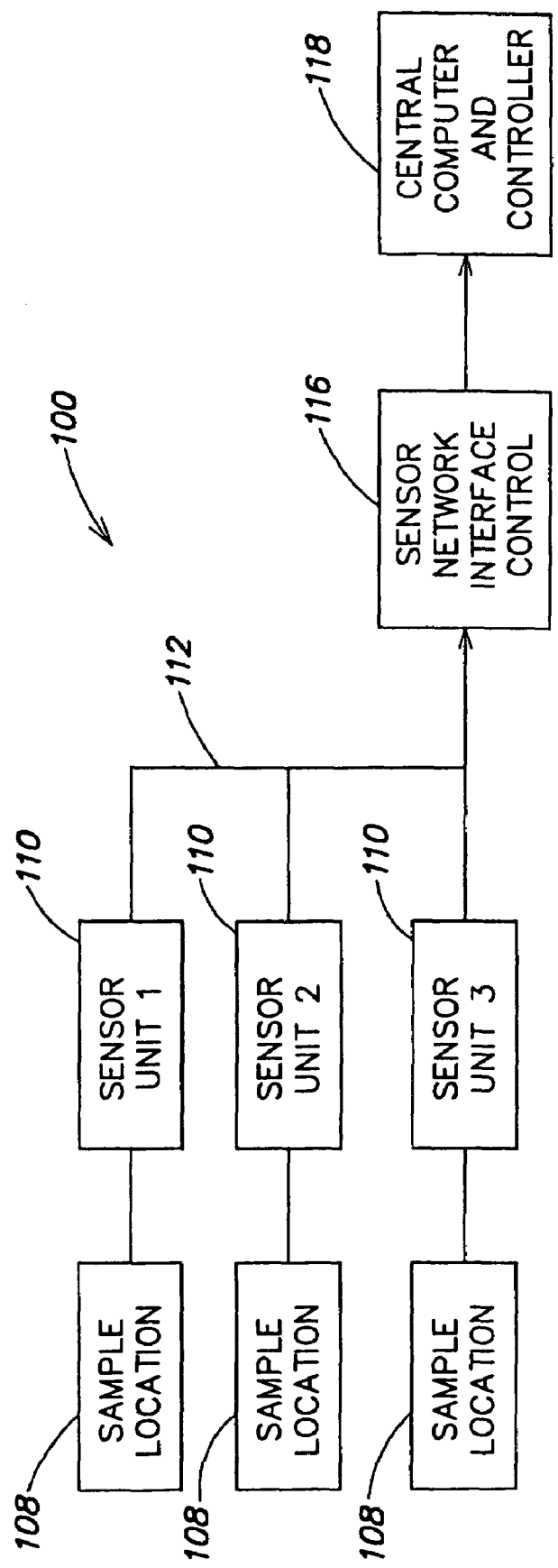
FIG. 2 is a schematic block diagram of an air monitoring system according to another embodiment of the invention.

An installed system may have many different configurations. The installed system may include an air monitoring unit 102 installed in a building to monitor one or more spaces within the building. Referring to FIG. 2, the installed system may use one or more sensor units 110 to monitor sample locations 108, where each sensor unit 110 has one or more sensors 104 for monitoring desired air quality parameters. Each sensor unit 110 may, for example, have the configuration of sensor unit 103 shown in FIG. 1. The sensor units may be distributed in desired locations inside and outside the building. The sensor units 110 connect through a network connection 112 to a central computer and controller 118. For example, as shown in FIG. 2, the sensor units connect to a sensor network interface control unit 116, which then connects to the central computer and controller 118. The central computer and controller 118 may connect to other equipment and interfaces as shown in FIG. 1. The network connection 112 used to connect the sensor units to the central unit may be a digital communication network of either proprietary design or open systems design such as a Lonworks or BACNet protocol. The network connection 112 may also be part of a building control network or part of an Ethernet system used for the building's information system communication network. A twisted pair network, an optical fiber, a power line, or wireless technology may be used for implementation.

FIG. 1 shows an implementation of the air monitoring system 100 where one sensor unit 103 is connected to control unit 106 through a sensor interface card 122 without need for a distributed digital network. This approach may be used for a portable air monitoring unit 102 to monitor one sample location 108, or may be used in an installed system to monitor many sample locations 108 with the addition of extra installed equipment that brings air from multiple sample locations to the air monitoring unit 102 in sequential fashion. A star based system of tubes and centrally located solenoid valves may be used to sequentially pull air samples from remote sample locations to the air monitoring unit. Alternatively, a networked air sampling system, as described in U.S. Pat. No. 6,125,710, may utilize a central backbone with branches to route multiple packets of air from multiple sample locations through the same backbone. Distributed switches, such as air solenoid valves, in the branches are controlled by a digital control network to bring air samples through the common backbone tube to the air monitoring unit, such that the packets of air may be monitored by the sensors 104 and the control unit 106 may store the air quality parameter data generated by the sensors.

For both the portable and the installed implementations, the air monitoring system 100, including the central unit 106 and the sensor unit 103, may be used in a portable fashion and may be moved from building to building to monitor different buildings or structures over time on either an as needed or on a periodic basis. For the installed system of FIG. 2, the central computer and controller 118 may be moved from building to building, and the distributed system components, such as the sensor units 110, may be installed permanently or semi-permanently. Typically in the system of FIG. 1, the air monitoring unit 102, including the sensor unit 103 and the control unit 106, may be moved from building to building, and the tubing and controls may be installed permanently or semi-permanently. As a consequence, at least the control unit 106 of FIG. 1, and the central computer and controller 118 of FIG. 2 may need to be reprogrammed and customized whenever the device is used to monitor a different building.

Referring to the air monitoring unit 102 of FIG. 1, the air to be sampled is first brought into a manifold 124. The manifold is an air conduit inside the sensor unit 103. From manifold 124, the air is routed to one or more sensors 104. The air may be routed using switches 342, such as solenoid valves or pumps or other such devices. As shown in FIG. 1, the manifold itself may contain sensors, such as on a manifold sensor card 126, to measure environmental or air quality parameters, such as temperature, humidity, barometric pressure or ozone level, which can change after the air enters the air monitoring unit. For example, as the air travels through the air monitoring unit the temperature may increase or ozone may react with the walls of the tubing in the unit, thereby reducing the accuracy of the measurement. These parameters are preferably measured soon after the air is brought into the air monitoring unit 102.

From the manifold, air may be routed to various sensors 104. As shown in FIG. 1, the air is routed to into a radon detector 128, a particle detector 132 and a grab sampling unit 130. The radon detector 128 may be a continuously detecting instrument that may use one of various methods for detecting the presence of Radon gas. One possible method is to trap air particles that may be contaminated by the Radon gas in a piece of filter paper next to a radiation softened DRAM memory chip. Daughter decay elements from the Radon gas that are trapped in the filter paper emit alpha particles into the memory chip. This memory chip is filled with data and any changes in the state of the data indicate that an alpa particle has hit the memory chip. The number of counts of these alpha particles over time gives a reading of the amount of Radon gas present in an area. Alternative approaches for measuring radon gas continuously, such as with Geiger detector type systems or other approaches, may also be used.

The particle detector 132 may use particle sensing or particle counting technology. Particle sensing systems are based on measuring air parameters that give an indication of the total mass of the particles in the air. Such systems may be based on ionization detectors as mentioned in U.S. Pat. No. 5,982,690 or mass based light scattering approaches, such as the DataRAM product manufactured by MIE Instruments of Bedford Mass. These products have been used in multiple parameter sensing instruments as mentioned in the above patent. Although these sensors are useful, it is becoming more apparent that from a health and safety standpoint that the number of particles, and in particular the number of fine particles under 2.5 microns, in size may be more relevant for indoor air quality measurements, since the smaller the particle the deeper into the lung the particle will go and the greater its potential health impact. In fact, recent medical studies have correlated the presence of large numbers of fine particles with increased occurrences of heart disease. Particle counting sensors are used to count the number of particles of a given size and can discriminate between different sized particles. As such, they are potentially more useful for indoor air quality monitoring in comparison to total particle mass sensors. Particle counting detectors typically operate by sending a small high speed stream of air through the beam of a laser diode. Light that is scattered, reflected or refracted by any particles in the subject stream of air is collected by various mirrors and optics and then measured by a sensitive light detector. The amount and magnitude of the pulses of light from the detector may then be used to count and sort the sizes of particles in the air stream. Other techniques may also be used to count the quantities of various size particles. Other sensors are available to count ultra-fine particles of size less than 0.1 microns such as the P-Track Model 8525 from TSI Inc. of St. Paul, MN.

The grab sampling unit 130 may include filter cartridges to capture particulate material and/or sorbent tubes to capture Volatile Organic Compounds (VOC's). Additionally, the grab sampling unit 130 may store air in Suma canisters, Tedlar bags or other inert storage canisters. The operation of the grab sampler unit 130 is explained in further detail below. Any type of sensor may be used in sensor unit 104, although as mentioned below sensors that use particles as part of the measuring process are preferably placed next in the air sampling path.

The air sample may be routed through only one sensor, no sensor via the bypass 343, which may include a switch 342, such as a solenoid or a pump, or may travel simultaneously in parallel through two or more sensors as controlled by the switch 342 as commanded by the central computer and controller 162. Since the radon and particle detectors' and grab sampling units' measurements are preferably based on a known quantity of air passing through the sensor, that the air flow may be accurately controlled through these sensors. Consequently an airflow sensor 344 may be used in series with the pump to measure the air monitoring unit's airflow. The pump's air flow rate can then be controlled via a variable speed pump control or some variable damper, orifice, or restriction device. The central computer and controller 162 or some other control unit such as an analog control circuit, located for example on the sensor interface card 122, may also be used to control the pump's airflow rate. If the pump's air flow rate is controlled and the flow rate is controlled through only one of the sensors 104, then their air flow rate is controlled. Moreover, if the air flow passes through two sensors simultaneously the split of air flow between these sensors may need to be fixed through some restrictive and potentially adjustable orifices or other flow adjusting device to accurately adjust the split of air between the two sensors. In this latter case, the air flow of the pump may be increased to set the air flow through these devices if two or more devices are operating in parallel. Alternatively, flow controlled pumps may be used for the switch 342 for controlling flow rate individually through each of the sensors 104. This flow rate control and balancing is not critical for the gas sensors 134 since their measurement is much less dependent on the flow rate through them.

Typically, the radon detector, particle detector or counters, and the grab sampling units are the next sensors to come in contact with the air sample after the manifold sensor and, since these sensors are detecting particulate matter in the air and fewer bends may avoid trapping and losing particles before these sensors. Additionally, filter 341 may be used in front of the gas sensors 134 to protect these sensors from being fouled by dust. Thus, these particle related sensors are typically provided in front of the gas sensors and dust or particulate filters. Additionally, these three types of sensors are not typically placed in series with each other. The air may pass through the particle detector, however some of the particles may be temporarily captured in the particle detector itself and released over time. Also, any bends in the tubing between sensors could cause particles to be lost in the tubing.

Air from the radon detector 128, particle detector 132 and/or the grab sampling units 130 may then pass into additional gas sensors 134, or the air may come directly from the manifold 124 to the gas sensors 134. The gas sensors 134 may include one or more sensors to detect gases such as carbon monoxide, carbon dioxide, Total VOC's (TVOC's), Nitric Oxide (NO), Nitrogen Dioxide (NO2), Ammonia, air acidity or alkalinity, specific VOC's such as formaldehyde, or any other gases that are of interest to the user of the system. After passing through the gas sensors, the air may pass through a filter 136, such as a HEPA particle filter or a gas filter, to remove hazardous or undesirable gases. Lastly, the air exits the system through an exhaust 138. A vacuum pump 140 may be used to pull air through the air monitoring unit.

Figure 3:
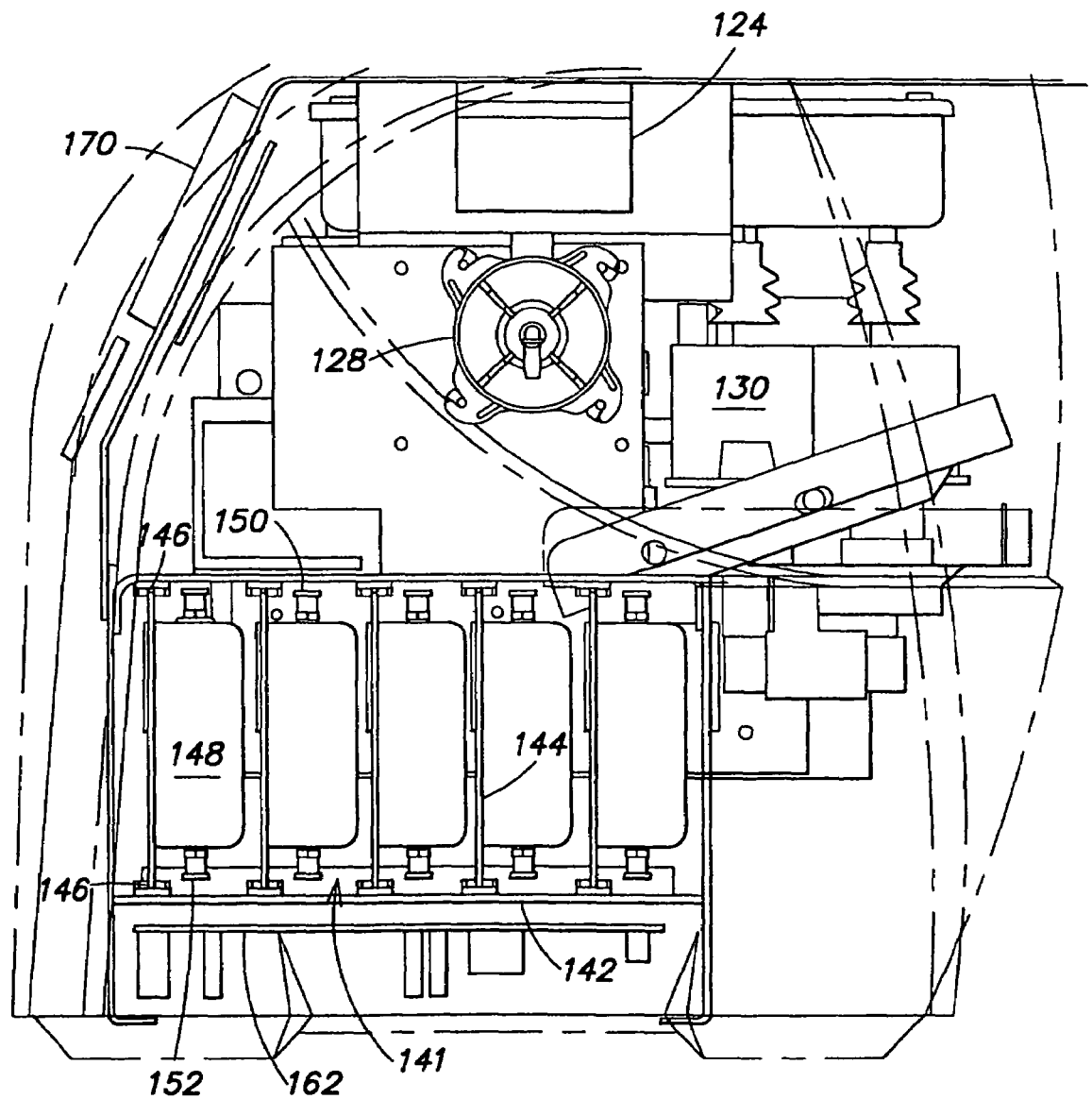
FIG. 3 is a cross-sectional side view of a portable air monitoring unit according to one embodiment of the invention.

An optional feature of the air monitoring unit described above is the use of a sensor bay or card cage 141 having removable cards to allow the easy and rapid reconfiguration of the air monitoring unit by a user to customize the air monitoring unit for a specific location or building. For example, a laboratory building requires different sensors, such as an air acidity sensor, from a classroom building where carbon dioxide is of greater importance for ventilation measurements. Preferably, a closed air path is provided to the sensors to minimize response time and to maintain sample integrity as the air moves through the air monitoring unit. As shown in FIG. 3, a card rack 142 is used to hold sensor cards 144. The sensor cards slide into the rack via slots 146 and are easily removable.

Figure 4:
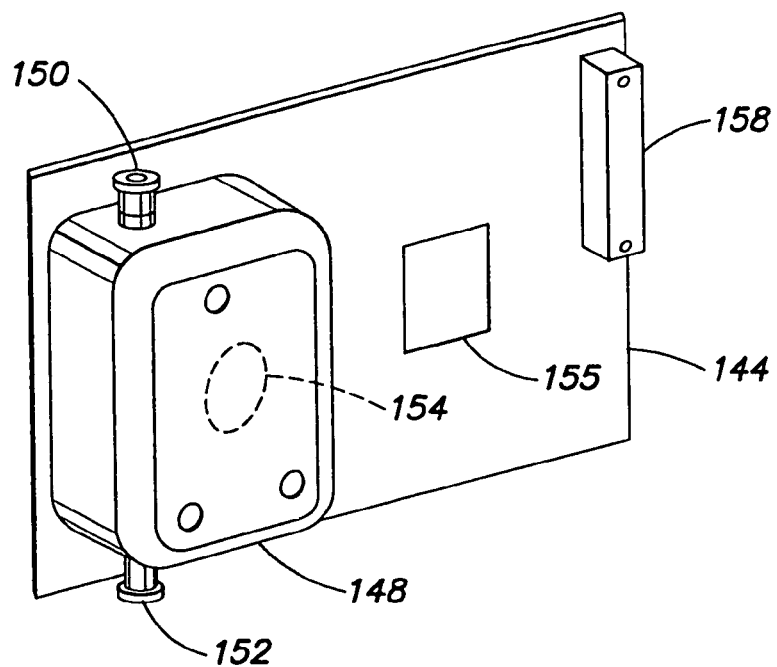
FIG. 4 is a front perspective view of a sensor card according to one embodiment of the invention.
Figure 5:
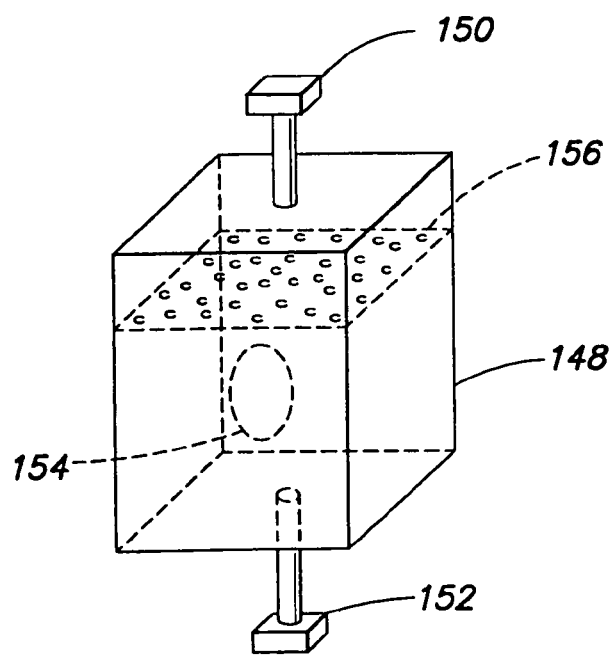
FIG. 5 is a perspective view of a shroud used on a sensor card according to one embodiment of the invention.

A sensor may include a sensing element 154 that is exposed to the air being monitored and sensor circuitry 155 or other components required for operation of the sensor. As shown in FIG. 4, the sensing element 154 and the circuitry 155 may be mounted on card 144. Sensor circuitry 155 may provide sensor signals to the central controller through a connector 158. A shroud 148 may be provided that substantially covers the sensor element 154 and defines an air flow path. The shroud 148 preferably has an intake port 150 and an exhaust port 152 to allow air flow through the shroud. The shroud 148 may form an air tight enclosure around the sensing element 154 to form a closed air path. Quick disconnect ports may be provided for the intake and exhaust ports 150 and 152 to facilitate installation and removal of the card. As shown in FIG. 5, a screen 156 or perforated plate may be mounted within shroud 148 to create a pressurized volume at the intake port that produces a laminar flow across the sensing element 154 to the exhaust port 152. The laminar flow from the intake end of the shroud 148 to the exhaust end creates a displacement ventilation effect and minimizes dead spots and recirculation inside the shroud. Air contaminants are thus flushed through the shroud 148 with minimal retention or capture by the shroud.

The removable sensor cards may use a standardized interface protocol and cable connector 158 as shown in FIG. 4, such that the cards can be quickly replaced in the air monitoring unit. To facilitate rapid setup of the unit, the information describing the type of sensor or multiple sensors on the card, in addition to calibration information and other pertinent information about the card can be stored on the card itself in nonvolatile memory. In this manner, the central computer and controller 162 through the sensor interface card 122 can immediately recognize and start taking data from the sensor card without need for user interaction or setup programming.

In a preferred embodiment, the sensor bay 141 includes a sensor interface board 122 in FIG. 1 to support electrical connections for the sensor cards within the sensor bay. The sensor interface board may recognize any sensor card that is plugged into the sensor bay. The sensor card may include configuration information, such as sensor type and calibration. The configuration information may be stored in an EEPROM on the sensor card, such as Microchip Technology's 25C320 EEPROM. Use of a computer for the sensor bay may not be necessary when using the EEPROM. The sensor interface board may read the configuration information in order to recognize the sensor and properly interface with the sensor card related sensor data interface. The configuration information and the sensor data interface are accessed using a serial bus connection, such as an SPI, provided at the connection of the sensor cards to the sensor bay.

A pin connector, provided at the electrical connections, may be used to connect the sensor cards to the sensor bay for power and communications purposes. A control pin on the pin connector may be a power enable pin. The logic signal provided on the control pin may be used to selectively enable power to be applied to the sensor circuitry 155 on each sensor card. Thus, the application of power to the sensors may be controlled, for example for power efficiency purposes. If the unit is operated on battery power, conservation of power may be useful. Moreover, some sensors may dissipate a relatively large amount of power, and it may not be desirable to run those sensors continuously. Furthermore, ambient temperature within the air monitoring unit may be reduced by selectively running the sensors. Power to each sensor may be controlled individually. The sensors may be turned on as needed and/or may be turned on at certain time intervals, such as every one or five minutes. Moreover, power to the sensor may be turned off and/or reduced to a lower level of consumption as desired.

Referring to FIG. 1, the control unit 106 stores the air quality parameter data measured by the sensors. The control unit 106 may also convert analog sensor data to digital data for storage. As shown in FIG. 1, a sensor interface card 122 may be used to convert the analog data to digital data for storage. The control unit 106 preferably includes a central computer and controller 162 that controls the functions of the air monitoring unit 102. Those functions may include, but are not limited to, controlling the flow of air through sensor unit 103 and acquisition of sensor data, storage of sensor data in some type of nonvolatile memory or storage media, processing sensor data to provide air quality information and communicating with a remotely located control center, such as a website 166. A local display 170 may be provided on the air monitoring unit 102. Preferably, the display 170 includes a touch screen, such that the user can input information into the control unit.

The air monitoring unit 102 performs data logging while keeping track of different locations of an air sampling sequence. A sampling sequence may be preprogrammed into the air monitoring unit 102. A preferred method of tracking the locations associated with the data logging process is to rely on the user of the air monitoring system to specify the locations before starting a sampling sequence. To enable this function to be performed in an intuitive way, the air monitoring unit is configured in advance with various customized user data. The customized data may be obtained when the user opens an air monitoring system account, such as through website 166. The website is designed to coordinate the user's account with the data that is communicated from the air monitoring unit 102 to the website. Data sent from the air monitoring unit 102 to the website 166 may include sensor data, air quality information derived from the sensor data, location data and/or any other data required for operation of the system.

The portable air monitoring unit 102 may incorporate a Global Positioning System (GPS) system 176. This allows the precise location of the air monitoring unit 102 to be determined. Use of GPS system 176 eliminates the need for the operator to input the air monitoring unit location each time the air monitoring unit is moved or to program a sequence of locations. Once the operator tells the unit the name of a given location the computer can correlate that name with GPS location information for that location so that subsequent testing of that location will be identified with it's appropriate name and data location. As a result, the monitoring location information is used to customize the air monitoring system, such that the resulting information from future testing of that location is associated with the specific building or room that is being monitored without need for further user input.

The air monitoring unit 102 may be connected to a local network or to the Internet 178. The connection of the air monitoring unit 102 to the Internet can be achieved in several ways using various communication media 180. A local connection into the building's data network, assuming the building has such a network, may be used. A common network in use within commercial facilities is an Ethernet system running at 10 MHz or more. Assuming this network has a connection to the Internet, the network may be used for access to the Internet. Another method is a local wireless connection involving a 900 MHz spread spectrum or other transmission technique commonly used in cordless phones. This technique utilizes a base unit transceiver that connects to a local phone line and another transceiver in the air monitoring unit 106. When the air monitoring unit needs to send or receive data, the unit checks the phone line to determine if it is busy, and if not the unit makes a call and sends or receives data through a local Internet Service Provider (ISP). Another method is to use a cellular phone to directly access a local or remote ISP. Finally, the air monitoring unit may connect to a building control system, which is connected to the Internet to provide data to the building control system for use by this system and to connect to the Internet. It will be understood that any method of connection to the Internet may be used.

As shown in FIG. 1, the website 166 may include remote web servers 182, a database 174, website programs and page generation software 172 and an expert system 186. The website 166 stores the air quality parameter data in the database 174 for recordkeeping and/or analysis. The data may be published on website 166 for access by the user via the account that the user sets up through the website and accesses through a computer and web browser 184.

The Internet may be used to download information to the air monitoring unit 102 to initialize or modify its program, operation, and/or setup based on specific information obtained about the building, its occupants, its surrounding environment and known or suspected problems. This customization of the unit may be achieved by expert system 186 located remotely in website 166 or, alternatively, in the air monitoring unit. Preferably, customization of the air monitoring unit 102 is achieved through the Internet. This aspect of the invention may involve the user answering questions about the building on the website. In particular, the user may utilize a user computer 184 to access website 166. The website may present to the user a series of questions, possibly determined by expert system 186, which permit the air monitoring unit 102 to be customized for a specific application. The questions may be a fixed set of questions, or questions later in the session may be modified depending on answers given earlier in the session. The information obtained from the user may be used to create a customized monitoring program to analyze a specific building. The program is downloaded from the website 166 through the Internet 178 into the memory of the central computer and controller 162 to control its operation. As air quality parameter data is acquired in and around the building, the program, operation and/or setup of the monitoring unit may be modified based on the acquired data. Non-expert system approaches may be used to customize or personalize the unit based on building specific information. However, the expert system 186 provides customization based on an expert system's ability to handle information in a way that simulates a human expert.

The expert system 186 may generate programs and parameters for operating the air monitoring unit and may analyze the results of the measurements with respect to a specific building or room. The expert system may include a program or a combination of programs that uses rule based, case based or pattern recognition methods, or a combination of these methods to analyze data and make decisions and recommendations based on user supplied information, environmental data, such as weather, and measured air quality parameter data. Alternatively, or in addition, the expert systems, sometimes referred to as artificial intelligence (AI) systems, may use fuzzy logic, neural networks or other AI techniques to analyze data or make decisions. The basis of the rules on which the expert system is founded may be a combination of knowledge supplied by experts or by experience that the expert system achieves through feedback as to the accuracy of its analysis or decisions.

The expert system may capture and automate the knowledge necessary to diagnose indoor air problems and to recommend solutions to those problems. The expert system, using reported complaints, may diagnose likely causes and possible remedies. The expert system may also assess the likelihood of complaints in the future, given the attributes of a building. The expert system, using a prior diagnosis, may recommend a testing/monitoring regime to improve or corroborate the prior diagnosis. Moreover, the expert system may use previous diagnoses and recommendations to provide an audit trail of feedback from the user as to the effectiveness of the expert system's conclusions and may factor this information into future diagnoses.

The expert system may accept different kinds of input, such as human observations and data transmitted from the air monitoring unit. Human observations may include information entered into the user's account. The expert system may function with either or both types of input.

Figure 6:
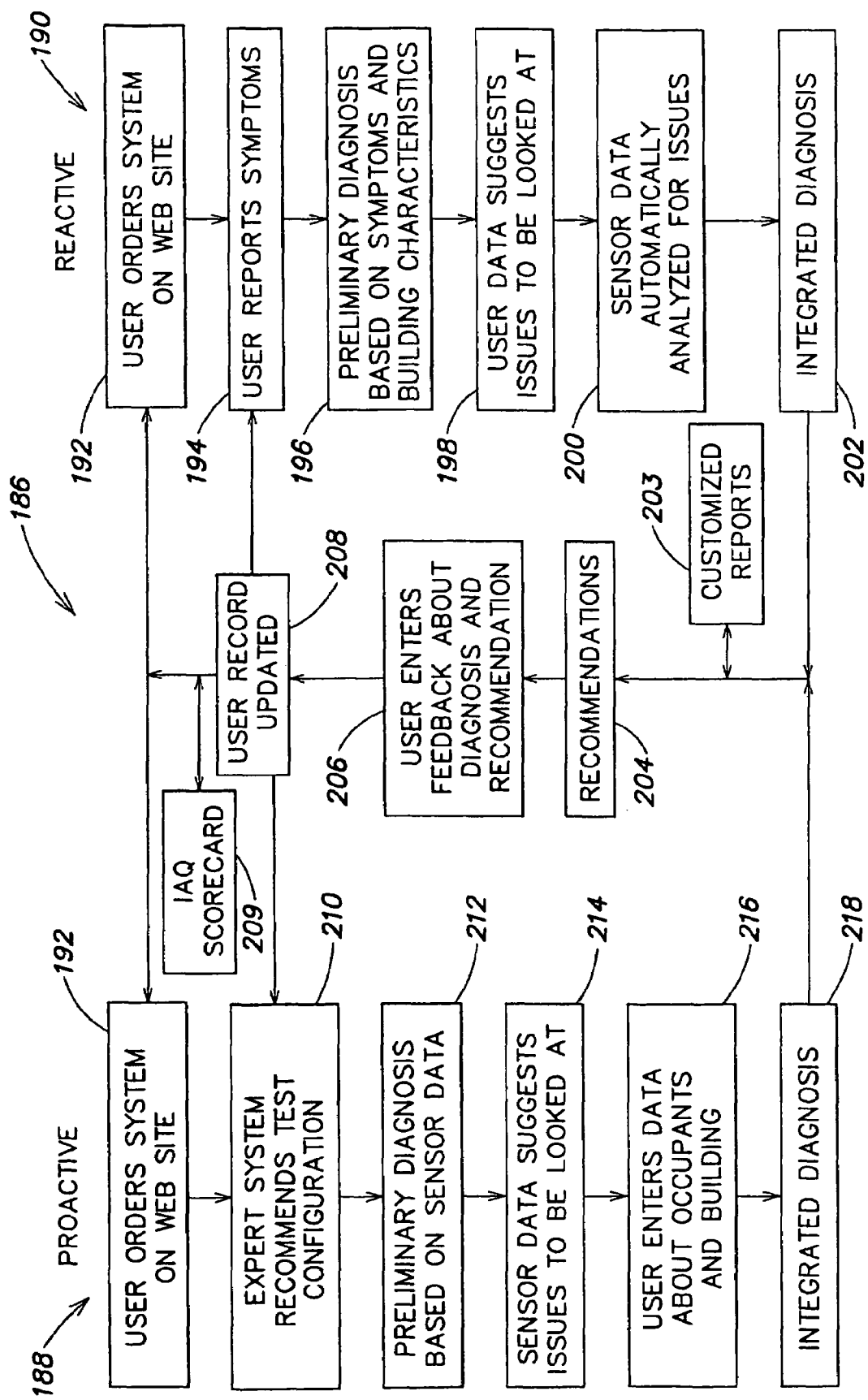
FIG. 6 is a schematic block diagram of an expert system according to one embodiment of the present invention.

Referring to FIG. 6, a flow chart of one embodiment of the expert system is shown. The expert system 186 is designed to act in a manner similar to a professional consultant. The expert system may proactively monitor 188 a structure for indoor air problems by controlling the air monitoring unit 102. The expert system 186 may also reactively diagnose 190 indoor air problems as suggested by symptoms disclosed by the user or occupant. When the expert system is operating in a proactive mode, data from the air monitoring unit may be utilized in the analysis. In contrast, information regarding symptoms may be more important in the reactive mode. The proactive and the reactive methodologies lead to diagnoses and recommendations. These activities are followed by an audit trail activity in which users report on the effectiveness of the recommendations. This feedback may be used to track user satisfaction and/or to provide input to an automated learning mechanism in the expert system. User records may be updated to reflect the inputs, diagnoses, recommendations, and feedback for an entire session.

The expert system 186 may configure the air monitoring unit 102 for testing a building or structure. Configuration regime variables include which rooms to monitor, the total number of rooms/floors to monitor, duration of sample collection, and whether allergen or special purpose tests should be conducted. The expert system 186 may recommend differential weightings on the different sensors. For example, the expert system 186 may recommend that certain sensors be given more airflow or sampled more frequently than others.

With either a proactive or a reactive methodology, the user first orders an indoor air analysis such as through the website 166 in step 192. When the expert system 186 is used in the reactive mode, a user or occupant may report symptoms in step 194, and then the expert system may generate a report issuing a preliminary diagnosis in step 196 on the likelihood that indoor air quality is causing those symptoms, as opposed to organic or other causes. The expert system 186 may also report the likelihood of specific kinds of causes, e.g., VOCs, Fungi, etc. Although symptom information drives the preliminary diagnosis of step 196, information about building characteristics, occupant characteristics, ongoing activities within the building, recent events and surrounding context can also be used. This information may be generated by having the user answer questions when opening their user account. The expert system 186 then suggests issues to be looked at in step 198 to help verify preliminary hypothesis generated in step 196. Sensor data is automatically analyzed relating to these issues in step 200, and an integrated diagnosis 202 is generated in step 202. Once the integrated diagnosis is generated, recommendations are made in step 204 for improving air quality in the building being analyzed.

The expert system 186 may also be used when symptoms aren't being experienced by building occupants. The expert system may provide a forecast of the future likelihood of indoor air-related symptoms within the building, given relevant information such as building characteristics, occupant characteristics, ongoing activities, events, and context.

In the proactive mode, expert system 186 may recommend a test configuration and procedure in step 210 that defines among other aspects, which areas to be tested, for how long, with what sensors, using which special grab sample tests, and under what conditions. The air monitoring unit may then issue a preliminary diagnosis in step 212 based on sensor air quality parameter data received from the air monitoring unit 102, and the expert system 186 suggests issues to be looked at in step 214 based on analysis of the sensor air quality parameter data. The user may enter data regarding the occupants of the building and the building itself in step 216 and an integrated diagnosis is performed in step 218. The expert system then makes recommendations in step 204 for improving air quality in the building being analyzed.

The expert system 186 may receive feedback in step 206 on the effectiveness of its prior diagnoses in steps 202 and 218 and its recommendations in step 204. The user's record is then updated in step 208. This feedback in step 206 may allow the expert system 186 to track a user over time and to therefore provide "customized" servicing of that user. Moreover, this feedback may drive an AI-based learning mechanism in which the expert system 186 alters its processing based on an assessment of its previous decisions.

The expert system 186 may contain many kinds of knowledge. One kind of knowledge the expert system may have is knowledge of the air monitoring unit 102 from which the expert system receives air quality parameter data. Since the expert system 186 knows about the air monitoring unit 102, the expert system may detect anomalies in the air monitoring unit and recommend self-checks on the air monitoring unit.

Sensor-driven air monitoring units, even when functioning perfectly, may occasionally send erroneous data. The expert system may be designed to know what kinds of data should be received and to detect when anomalous data is present. It is also possible for users to "game" the air monitoring unit, e.g., by breathing into it or by sending cigarette smoke directly into it. The expert system may be able to detect these kinds of situations as well. When the expert system detects tampered or faulty data, the tampered or faulty data may be discarded. If data is missing, the missing data may be filled in with average values or ignored.

Figure 7A:
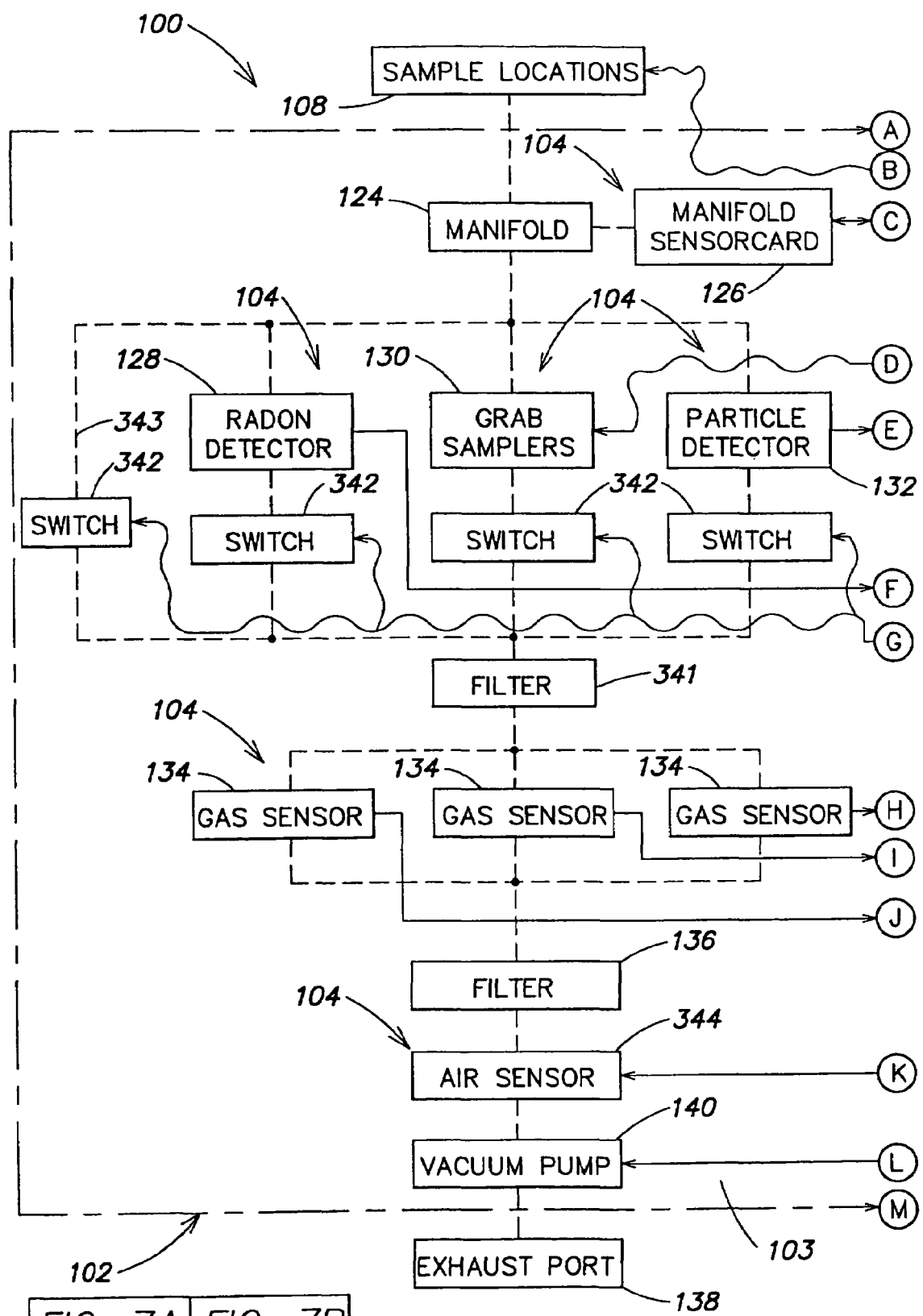
FIG. 7 is a schematic block diagram of an air monitoring system according to another embodiment of the invention.
Figure 7B:
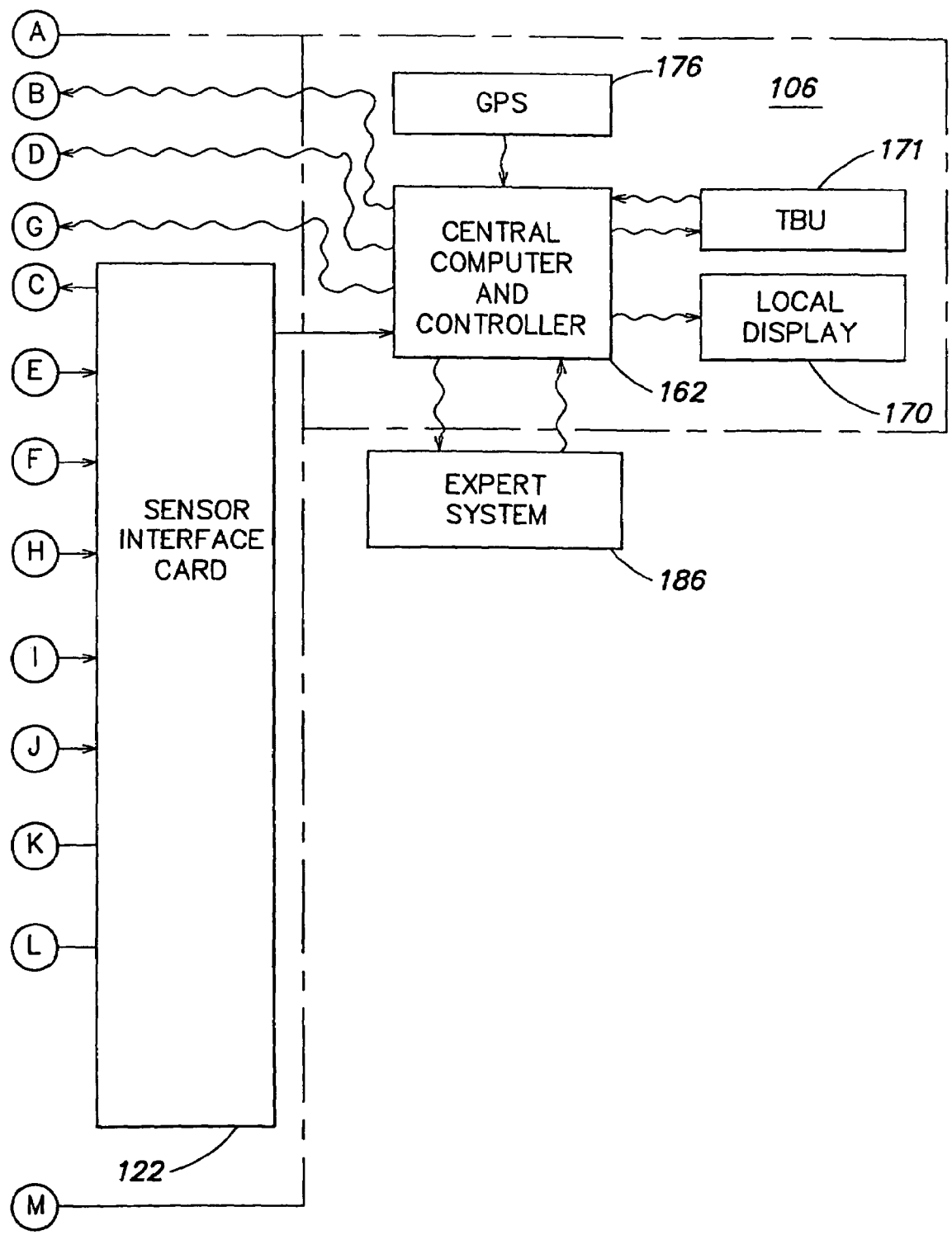

Referring to FIG. 7, the expert system 186 is shown connected to the control unit 106 of the air monitoring unit 102. As shown, the expert system may be provided locally within the control unit.

The expert system may be "self-contained". The expert system may be embedded within a series of web pages, but still may not be part of the main website and may be a mini-website relative to the main site. The mini-website of the expert system 186 may have its own IP address and may be invoked directly from a Web browser. Preferably, controls may be put in place to prevent the mini-website from being accessible under normal circumstances. Instead, it is preferable that users interact with the main website and request expert system services as desired. One or more databases may support the expert system. The databases may hold data regarding an occupant, a building, current and historical air monitoring data and previous diagnosis, recommendations and user feedback, as well as other associated variables pertaining to a user.

The expert system may use any type of reasoning apparent to one of skill in the art, such as deductive reasoning, reasoning by analogy and fuzzy reasoning over patterns. With deductive reasoning, the expert system may infer the likelihood that various indoor air problems exist, given user data. Deductions may occur along a chain of "if-then" rules, the rules being the standard form of knowledge representation within expert systems. When using reasoning by analogy, the expert system may consult a database of standard Indoor Air Quality (IAQ) cases and find those cases that are similar to that of the user. This kind of reasoning is called "by analogy" or "case-based" and the knowledge that underlies it "cases". With fuzzy reasoning over patterns, the expert system may consult a library of anomalous patterns and compare those patterns to the air quality parameter data and grab samples. IAQ problems are inferred to exist within the data to the extent that the anomalous patterns fit the data. Perfect fits are not expected. The degree to which the patterns fit the data using techniques of fuzzy set theory are assessed.

All three types of reasoning or expert may exist separately or together for a given user. Each type of reasoning results in a probabilistic assessment of IAQ problems within user and sensor data. The results of each assessment under each type of reasoning may be combined into an overall assessment. This integration occurs via an AI architectural technique known as "Blackboarding". A blackboard is an event-driven data structure. The purpose of the blackboard is to allow each of the three reasoning methods to "post" its intermediate results to a common locale. In this way, each reasoning method can use the results of the other two methods, if desired. Other reasoning methodologies may be added to the expert system.

The expert system 186 may use the Web session as the "Blackboard". Results from all the reasoning methodologies, which are commonly referred to as "experts" are posted to the Web session and are available for use by the other experts. Use of the Web session as the expert system blackboard is possible due to the use of AI libraries to model expertise, such that common I/O operations run across libraries, meaning that different experts can speak to each other even if they use different knowledge representation techniques. Objects may persist across Web pages, such that the blackboard persists throughout the Web session. The Web session may opportunistically poll experts for answers, based on the dynamic gathering of information.

The expert system may employ the knowledge of multiple experts or reasoning methods. These experts, due to the different methodologies they employ, may bring a diverse set of perspectives to the problem of assessing air quality. Thus, the expert system may be designed to incorporate multiple, cooperating experts, each of whom is expert yet approaches the same problem in different ways. From a process standpoint, each expert may be assigned to work on the entire indoor air quality problem versus having a different part of the problem be worked by a different expert or methodology.

The exact sensor patterns that are diagnostic of IAQ problems may be revealed from the data itself and added to the library of anomalous patterns that are specified analytically. To effect this, the expert system may contain a data mining capability. User data, such as air quality parameter data, may be mined for significant patterns, and when such patterns are deemed to exist, they may be incorporated into the live expert system. Typically, this would not affect the use of the expert system, such as having to shut the system down to rebuild. Data that has previously been compared to the expert system pattern library may be reanalyzed with new patterns, making the system appear smart as well as providing new insights into nagging customer problems.

Data mining is typically coupled with a learning mechanism. The expert system may mine for all new patterns but may only "learn" those patterns that are diagnostic of indoor air problems. For example, the audit trail facility in which users give feedback on prior diagnoses in step 206 acts as a "teacher". In other words, the expert system may mine for new patterns and may correlate all mined patterns with feedback given by users. Mined patterns that are correlated with assertions of "good" diagnoses may be learned, while patterns that are correlated with feedback of "bad" diagnoses may be forgotten. The learning mechanism goes beyond sensor air quality parameter data patterns. In fact, all three kinds of knowledge—rules, cases, and patterns—may be learned over time. For each of the three types of knowledge, user feedback may act as a "teaching" mechanism.

The expert system 186 may form the foundation of an IAQ scorecard 209. This scorecard may be analogous to the scorecards used by the mortgage industry. Within the mortgage industry, loan originators, the secondary mortgage market, and credit rating agencies all use scorecards to assess the credit worthiness of loan applicants. Scores produced by such scorecards are weighted combinations of credit attributes and therefore are a single number that represent credit worthiness. In a similar manner, an IAQ Scorecard may have a weighted combination of IAQ attributes. An example of an IAQ scorecard might include three subindices. The first may be a rating of comfort and ventilation using such parameters as temperature, relative humidity, and CO2. A second may be a measure of the healthiness of the space or conversely the level of pollutants or contaminants in the air. This measure may involve measurements of gases such as carbon monoxide, VOC's, allergens, mold, etc. A third area may be used to cover operational issues such as energy efficiency or the usage of outside air. These areas or others may be used individually or combined in some weighted manner to create a single number index. The attributes and their weights may be guessed at prior to collection of data but most likely will be determined empirically. As such, the expert system's data mining and learning capabilities may be critical to the construction of a scorecard that truly distinguishes "IAQ bad risks" from "IAQ good risks". Finally, the IAQ scorecard may also take the numbers that are generated and aggregate them with other similar numbers. After a large enough database is generated, each individual user's IAQ score can be compared to others to generate a percentile result of how the particular analyzed building or room compares to other buildings within the same area or across the country. Since there are no official guidelines on IAQ parameters, this kind of comparative analysis or score can be useful to know how a facility is doing relative to other similar buildings in providing good air to its occupants. The expert system may then also recommend approaches based on a low score that should allow a building's score to be raised.

One application of the air monitoring unit 102 involves rental or lease to the general public, and this embodiment is discussed in detail below. Specifically, the application of a portable air monitoring unit 102 as shown in FIG. 1 is discussed. Over time, a unit may be assigned to many different users. Alternatively, one user who owns or rents the air monitoring unit may use it in multiple buildings or locations, or a service organization may use the air monitoring unit to provide indoor air quality audits for many different users. To support these functions, the air monitoring unit 102 may be designed to have its user information erased after each use. At the onset of commissioning, the air monitoring unit may contain only generic configuration information, such as sensor calibration data. Configuration data, such as information in the user's account database, may be downloaded to the air monitoring unit 102 once the unit is in the user's possession. This configuration information is preferably downloaded to the air monitoring unit via the Internet. The air monitoring unit 102 takes on a "personality" that reflects the profile of the specific user's building and/or occupants. Any questions relevant to the evaluation of the indoor air quality for the building may be answered by the user on the website via the user's computer 184. The user's answers are located in the user's account, and are accessible by the website program 172 and expert system 186. Such questions may include questions about the building, the occupants and the building's surroundings. Many possible questions will be apparent to those of skill in the art. If the user is a homeowner, this configuration information may include customized room names assigned to a table of room numbers, as shown in Table 1 below.

TABLE 1

| Room 1: | Basement |
| Room 2: | First Floor Bathroom |
| Room 3: | Sally's Room |
| Room 4: | Living Room |
| Room 5: | Kitchen |

TABLE 1-continued

| Room 6: | My Office Room |
| Room 7: | My Bedroom |
| Room 8: | My Bathroom |

As air quality parameter data is transferred from the air monitoring unit 102 to the user's account database 174 via the Internet 178, the data in the database may be associated with the customized names. This enables the user to easily interpret the data when viewing the data on the website 166. The website 166 may generate customized reports 203 on the user's indoor air quality that may be displayed on the website and may also be printed out in hard copy form off a printer. For example, if the data recorded for Room 3 shows that VOC levels are high, a personalized report can be generated that specifically says "the VOC levels in Sally's room are high".

Another benefit of configuring the air monitoring unit 102 with customized information is that it may substantially simplify the administration of the air sampling tests if the air monitoring unit is portable. The air monitoring unit 102 presents to the user prompts that can be readily understood. For example, once the air monitoring unit is configured with the customized information, air sampling sequences can commence based on a predetermined script by room number. However, the user may be prompted based on the customized name assigned to each room number. Therefore, once the monitoring process for Room 1, the "Basement", is complete, the air monitoring unit 102 can prompt the user to relocate the unit to the "First Floor Bathroom", or Room 2. This enables the air monitoring unit 102 to be moved around the building in a relatively foolproof manner. If a GPS system 176 is included in the air monitoring unit, the GPS system can thereafter verify the location of air monitoring unit 102 in a particular room.

The implementation of the air monitoring unit 102 may be driven by the user's account, which is established by the user via the internet. Because the air monitoring units that may be rented will serve numerous customers, it is preferable that the method used to transfer the air quality parameter data to the user's account be highly reliable and secure. This may reduce the possibility of the accidental transfer of data to the wrong account, such as the account of the previous user. A preferred way of achieving reliability and security is to supply the user with a unique I.D. number after they open a user account via the Internet. This I.D. number is input into the air monitoring unit 102 by the user before the air monitoring unit accesses the Internet to obtain the personalized data from the user's account. An account name may be included with the I.D. number to further reduce the potential for accessing the wrong user account. Encryption of the communication between the air monitoring system 102 and the website 166 can provide additional security.

Since one of the basic functions of the air monitoring unit is to periodically and automatically upload sampled air quality parameter data to the user account via the Internet, the mechanism by which the unit accesses a phone line should be highly flexible. The data transfer process to the Internet is preferably transparent to the user, as it would be highly inconvenient for the user to be manually involved in the process, given the frequency of the activity. The data transfer process may occur once an hour, or more or less frequently, depending on the nature of the application. One reason for such frequent data transfer is that the air quality parameter data may be used to provide rapid feedback to the user. A rapid response in the presentation of air quality parameter data from the air monitoring unit 102 can be useful when the user is trying to determine the effectiveness of a change being implemented to remedy an air quality problem. For example, the user may want to assess the effectiveness of the application of a portable air cleaner to a room in the building.

To support the transparent transfer of data to the Internet, a preferred embodiment of the air monitoring unit 102 includes a wireless data link to a phone line. Alternatively, a wireless data link to a building Local Area Network may be used. The method involves a second unit, the Telephone Base Unit (TBU) which is designed to physically connect to a phone jack and to provide 900 MHz wireless communications to the air monitoring unit 102. This allows the air monitoring unit to "dial out" any time the phone line is available, while the unit is located in the building under evaluation.

In order to initially configure the air monitoring unit 102, the user plugs the air monitoring unit into a power source. The air monitoring unit may be battery powered. The user would also connect a power source to the telephone base unit 171 (TBU), if it is not battery powered. At this point, when the air monitoring unit and TBU are being configured for use, the user may connect the TBU to an available phone line. As is the case with most modems, the TBU may have an RJ11 jack to allow the phone line connection to be shared between the TBU and some other device, like a telephone.

The user initiates a Test and Configuration Mode via the air monitoring unit touch screen display 170. The air monitoring unit 102 tests communications locally between the air monitoring unit and the TBU. When the phone line is free, the TBU dials out via a toll free number to an Internet Service Provider. The air monitoring unit 102 sends the unique I.D. number for the user and links to the customer's database on the website 166. The website 166 downloads information, such as a program and parameter information, so as to configure the air monitoring unit 102 for performing a test or a series of tests in a specific building. Thereafter, the commissioning process is complete, and the air monitoring unit 102 is ready for use. The user places the air monitoring unit in a desired location and selects the room to be tested using the touch screen display. The unit may verify the signal strength, and the unit may be relocated if the signal is poor. Alternatively, the unit may store air quality parameter data for later uploading to the Internet when the unit is moved back within range of the TBU. An Air Sampling Mode is initiated, and local data is displayed on the touch screen display. Air quality parameter data is transferred to the website 166 on a periodic basis, such as once per hour or as frequently as desired, and the air monitoring unit may be reconfigured or information may be downloaded to the unit.

The air monitoring system may be configured to capture samples of air based upon the detection of various events that may be associated with indoor air conditions. The capability of triggering the capture of an air sample at a precise moment is helpful to diagnose and eventually resolve an indoor air quality problem, as these problems are often transient in nature.

Figure 8A:
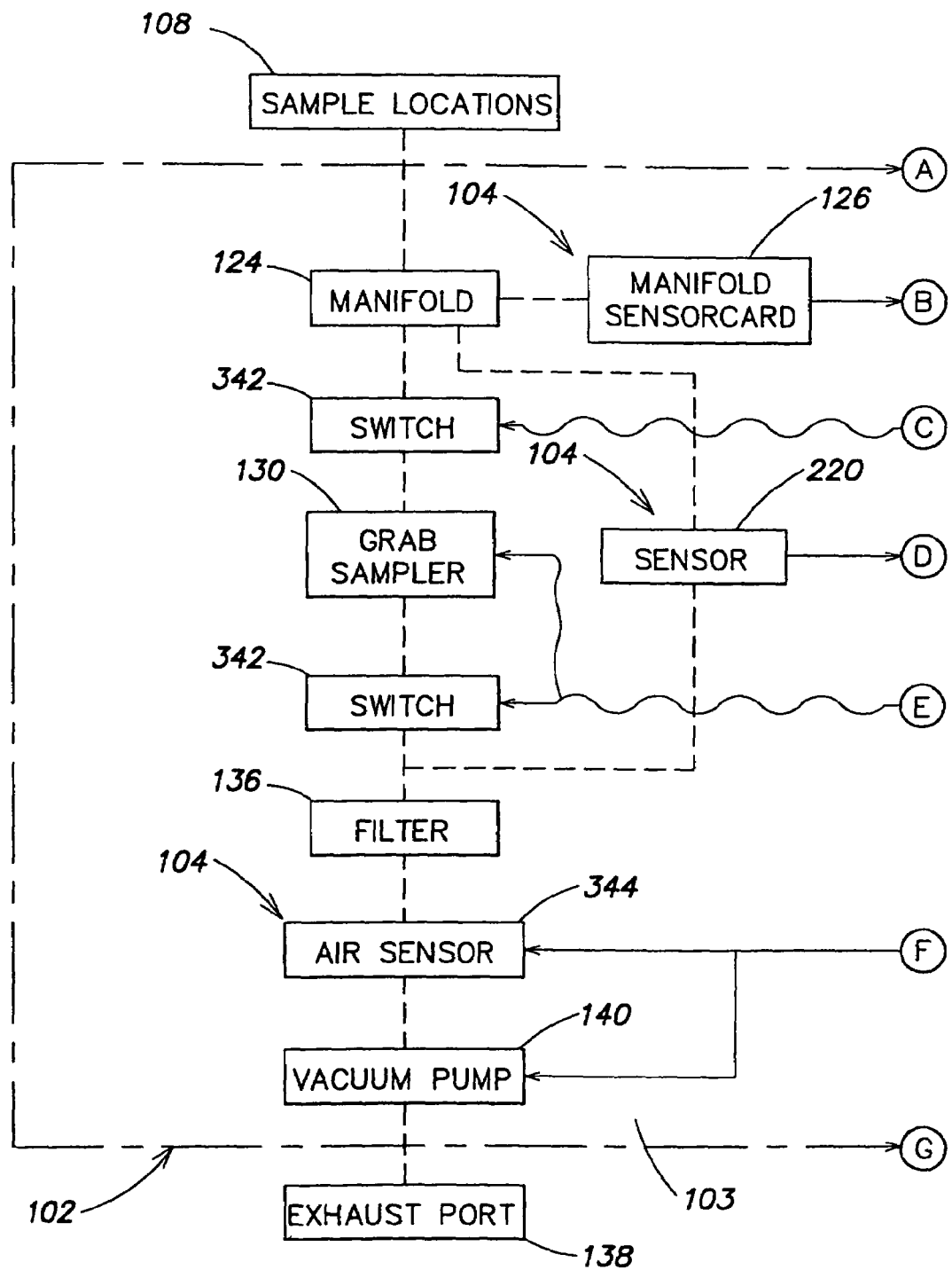
FIG. 8 is a schematic block diagram of an air monitoring system including a grab sampler according to one embodiment of the invention.
Figure 8B:
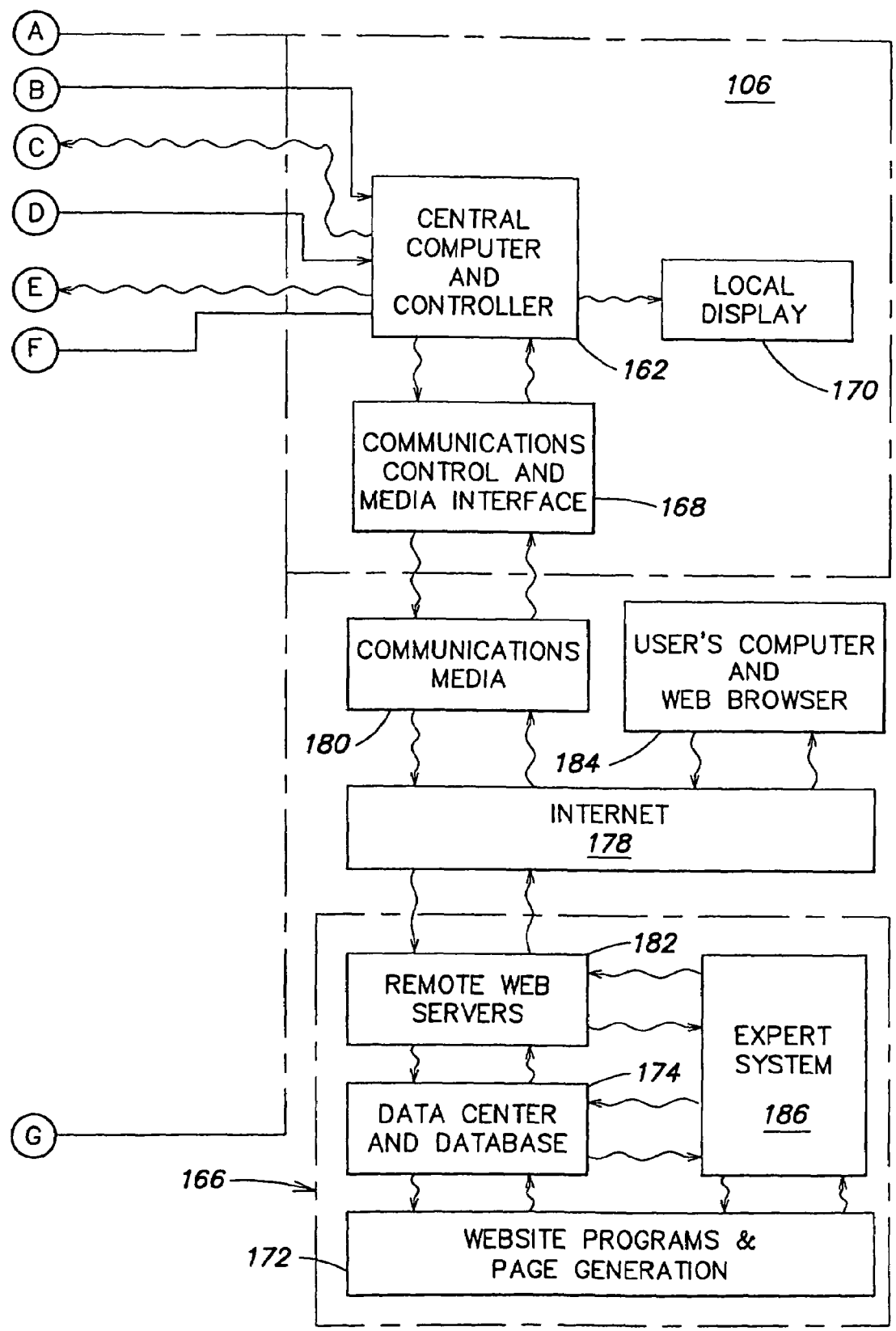

As shown in FIG. 8, air monitoring unit 102 may include a continuous or periodically sampled air parameter sensor 220 and grab sampler 130. The taking of a sample by grab sampler 130 may be triggered by the air monitoring unit 102 itself, based on monitoring by the air parameter sensor 220. Alternatively, the air parameter sensor 220 may be monitored by the website 166 through the Internet. A command transmitted from the website 166 through the Internet 178 to the air monitoring unit 102 may trigger the capture of an air sample so that a more detailed analysis of the air quality parameter can be performed. In either case, the taking of the grab sample is triggered when the parameter sensed by sensor 220 meets a predetermined criteria. It will be understood that the criteria for triggering the taking of the grab sample can be based on measurements by two or more sensors and/or on other information.

One embodiment of the invention involves using a broad sensor, for example a sensor used to detect Total Volatile Organic Compounds (TVOC's), as the measurement device or the air parameter sensor 220 from which the taking of a grab sample may be triggered. By monitoring such a sensor, a grab sample can be triggered based on the presence of any one of a large number of VOC parameters to which the sensor is sensitive and/or at a predetermined concentration. In such an application, the "grab sample" device may be a sorbent tube filled with Tenax-G or Carbosieve-3 absorption material. The sorbent tube may be removed from the grab sampler after a sample has been taken and sent to a laboratory for analysis. The results can then be put into the user's website account and the expert system used to analyze this information in the context of other collected data and information.

Another embodiment involves the capture of particulate matter, using a particle sensor as the air parameter sensor 220 and a filter cartridge, auger plate, petri dish, "sticky slide" or particle impaction device as shown in U.S. Pat. No. 5,693,895, or other suitable device on which to deposit a particulate sample in order to capture a sample for analysis. This approach uses the particle sensor to track the concentration of particulates in the indoor environment. The criteria for triggering a grab sample may include concentrations above the average concentration, above a predetermined threshold value, and/or by way of decisions made by an expert system on various user supplied information, and real time data, such as particle concentration data from the sensor. Grab sampling of particulate matter is a practical way of testing for mold, bacteria, and other viables, as well as pollen, dander, and other types of allergens. As is the case with grab sampling using sorbent tubes, grab sampling for particulate matter using the trigger mechanism allows events to be captured as they happen. For example, mold within households can create miserable conditions for inhabitants, yet these conditions may be present for short periods of time based on fluctuations in humidity. Therefore, identifying a mold problem and the type of mold present can be difficult unless the symptoms are persistent. However, a trigger based sampling method that captures mold spores while still in flight may provide conclusive evidence of the problem. This is especially true, given the fact that the samples captured on the filter or auger plate can be analyzed by a laboratory to identify the concentration and species of mold, pollen, etc. that was captured.

More generally the concept of utilizing an air parameter sensor 220 to trigger a grab sample may apply to any sensor deployed to monitor a parameter or parameters of interest and may involve any type of suitable mechanism to trap a sample. For example, the grab sample may utilize absorption material, filter media, a canister, a particle impaction device or an Auger plate, but is not limited to these devices.

Another embodiment of the invention involves triggering a grab sample using the senses and general perceptions of the occupants that are exposed to the environment being monitored. Since indoor air quality is generally monitored for the sake of the occupants of an environment, their observations may be used to trigger the taking of a grab sample. Indoor air quality may often be falsely blamed as the source of an occupant's discomfort or health problems. For example, if an occupant becomes drowsy when he or she is present in a particular location of a building for any given duration, poor indoor air quality may be suspected as the cause of discomfort. In this embodiment, an input mechanism is provided for occupants to initiate a timely air sample of that environment, based on their observations. Such samples can help to rule out indoor air quality as the source of the problem observed by the occupant.

When deployed in an office building or other commercial environment, a preferred method of triggering the taking of an air sample involves the utilization of the local area network (Intranet) in that facility. The air monitoring unit is connected to the local area network. A software application installed on each personal computer in the building permits the occupants, via the local area network, trigger the taking of a grab sample.

Alternatively, the Internet may be used by a facility manager or other management professional to remotely trigger the taking of a grab sample via the air monitoring unit 102 based on reports of complaints from workers in the building or a location within a building. The responsible manager may immediately, upon being informed of the problem, log onto the appropriate user account at website 166 and trigger a grab sample by a command transmitted via the Internet to the air monitoring unit 102. Use of the Internet allows anyone with authorization to trigger a grab sample by the unit at any time from any location, without need for more than a standard web browser and Internet access.

In smaller scale air sampling applications that do not lend themselves to a networked strategy using an installed system, such as in a home, taking of air samples may be triggered by the user directly on the air monitoring unit 102.

The following are some other practical trigger sources that can be used to trigger a grab sample. A time or date schedule can be used. For example, a grab sample may be triggered at the same time each day, or periodically throughout the course of a day. This may be helpful in establishing a detailed baseline on the parameters present in a building over time. Also, if performed frequently enough, transients in concentrations of specific parameters over a short period of time can be identified.

A significant event noted by another system in the building may be used to trigger a grab sampler. For example, it may be useful to obtain one or a plurality of grab samples throughout the building in the event that a fire alarm is triggered, as fire alarms are in some cases triggered when there is an accidental spillage of a toxic material. Grab sampling in such a case may assist in providing a record of the levels of exposure realized throughout the building for a given time.

A security alarm may be used to trigger a grab sample or a strategic number of grab samples under certain cases where it is thought that a breach of entry could be associated with a chemical or biological attack. Sampling for such parameters may be of importance to airports, government buildings, and other public places that are concerned with terrorism.

Emergency conditions in laboratory and other critical environments may be used to trigger a grab sample. This includes wet chemistry and biological laboratories, the exterior surroundings of fumehoods and biological safety cabinets, vivariums, hospital isolation rooms, potent compound and tableting areas, as well as other pharmaceutical environments. For example, if a laboratory's ventilation system were to fail, due for example to a loss in supply or exhaust system pressure, the alarm condition noted by that system may be coupled to the grab sampler so as to trigger the capture of air samples. The significance of this activity, among other things, would be to establish if there has been a breach of containment of air quality parameters at a dangerous level. This may be very valuable information to counter potential future legal claims of wrongdoing against the owner of such a facility.

Central to each embodiment described is the added concept of providing capabilities of taking a plurality of samples over the course of time without need for manual intervention. This entails a mechanism that may support a number of media for grab sampling that may either automatically or manually be marked for tracking and cataloging purposes.

Although the present invention is described with reference to certain preferred embodiments, it will be appreciated that numerous modifications and other embodiments may be devised by those skilled in the art. For example, an expert system may be provided within the air monitoring unit locally and may access the database on a website via the Internet to analyze the data and make appropriate changes to the configuration of the air monitoring unit. Therefore, it will be understood that the appended claims are intended to cover all such modifications and embodiments which come within the spirit and scope of the present invention.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A method of making comparisons of indoor air quality (IAQ), comprising the steps of:
    collecting indoor air quality data for at least two different air quality parameters from at least two distinct locations;
    using an expert system to determine weights to be applied to each of the air quality parameters, apply the weights to the parameters, and combine each of the weighted parameters from a location into an IAQ score for that location;
    storing the IAQ scores in a database; and
    comparing the stored IAQ scores to one another.

2. The method of claim 1, wherein the step of collecting data comprises measuring various air quality parameters.

3. The method of claim 2 wherein the step of collecting data further comprises sending collected data to the database via a public network.

4. The method of claim 2 wherein the step of collecting data comprises collecting data from at least one sensor selected from the group of sensors consisting of a carbon dioxide sensor, a particle sensor, a humidity sensor and a temperature sensor.

5. The method of claim 4 further comprising determining a rating of comfort and ventilation at a location using data from at least a carbon dioxide sensor, a temperature sensor and a humidity sensor at the location.

6. The method of claim 2 wherein the step of collecting data comprises collecting data from at least one sensor selected from the group of sensors consisting of a carbon monoxide sensor and a volatile organic compound (VOC) sensor.

7. The method of claim 6 further comprising determining a measure of pollutants at a location using data from at least a carbon monoxide sensor and a VOC sensor at the location.

8. The method of claim 2 further comprising determining a rating of energy efficiency or the use of outside air.

9. The method of claim 1 wherein the weights are determined empirically.

10. The method of claim 1 wherein the comparing step comprises generating a result of how the IAQ score of a location compares to the IAQ score of other locations.

11. The method of claim 10 further comprising using the expert system to make ventilation recommendations based on the result.

12. The method of claim 11 wherein the recommendations allow the result to improve.

13. The method of claim 10 in which the result is a percentile result of how the IAQ score of a location compares to the IAQ score of other locations.

14. The method of claim 10, further comprising combining the IAQ scores from a plurality of distinct locations to create a multiple location index that is representative of more than one location.

15. The method of claim 14, wherein said multiple location index is representative of the indoor air quality of an entire building.

16. The method of claim 14, wherein said multiple location index is representative of the indoor air quality of a portion of a building.

17. The method of claim 1 wherein the distinct location are separate buildings.

18. A method of making comparisons of indoor air quality (IAQ), comprising the steps of:
   collecting indoor air quality data for at least two different air quality parameters from at least two distinct locations by measuring various air quality parameters using at least one sensor selected from the group of sensors consisting of a carbon dioxide sensor, a particle sensor, a humidity sensor and a temperature sensor;
   using an expert system to determine weights to be applied to each of the air quality parameters, apply the weights to the parameters, and combine each of the weighted parameters from a location into an IAQ score for that location;
   storing the IAQ scores in a database;
   comparing the stored IAQ scores to one another and generating a result of how the IAQ score of a location compares to that of other locations; and
   using the expert system to make recommendations based on the result.

19. A method of making comparisons of indoor air quality (IAQ), comprising the steps of:
   collecting indoor air quality data for at least two different air quality parameters from at least two distinct locations by measuring various air quality parameters using at least one sensor selected from a first group of sensors consisting of a carbon dioxide sensor, a particle sensor, a humidity sensor and a temperature sensor, and at least one sensor selected from a second group of sensors consisting of a carbon monoxide sensor and a volatile organic compound (VOC) sensor;
   using an expert system to determine weights to be applied to each of the air quality parameters, apply the weights to the parameters, and combine each of the weighted parameters from a location into an IAQ score for that location;
   storing the IAQ scores in a database;
   comparing the stored IAQ scores to one another and generating a result of how the IAQ score of a location compares to that of other locations;
   using the expert system to make ventilation recommendations based on the result;
   determining a rating of comfort and ventilation at a first location using data from at least a carbon dioxide sensor, a temperature sensor and a humidity sensor at the first location; and
   determining a measure of pollutants at a location using data from at least a carbon monoxide sensor and a VOC sensor at the first location.

* * * * *